(12) United States Patent
Grandt

(10) Patent No.: US 8,591,565 B2
(45) Date of Patent: Nov. 26, 2013

(54) PROCESS FOR LOADING A STENT ONTO A STENT DELIVERY SYSTEM

(75) Inventor: Axel Grandt, Strassberg (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 97 days.

(21) Appl. No.: 13/133,930

(22) PCT Filed: Dec. 11, 2009

(86) PCT No.: PCT/EP2009/008886
§ 371 (c)(1),
(2), (4) Date: Oct. 20, 2011

(87) PCT Pub. No.: WO2010/066446
PCT Pub. Date: Jun. 17, 2010

(65) Prior Publication Data
US 2012/0035704 A1   Feb. 9, 2012

(30) Foreign Application Priority Data
Dec. 12, 2008  (EP) ..................... 08021665

(51) Int. Cl.
*A61F 2/06* (2013.01)

(52) U.S. Cl.
USPC ........................................ 623/1.11

(58) Field of Classification Search
USPC ............ 29/464, 515, 516, 517, 521; 264/249, 264/293, 320, 322, 340; 604/96.01, 604/99.01–99.02, 101.02–101.05, 604/102.01–102.03, 103–103.14; 606/191–195, 198, 108; 623/1.11, 623/2.11, 1.13–1.17, 1.22–1.37, 1.42–1.54, 623/909, 920, 921

See application file for complete search history.

(56) References Cited

U.S. PATENT DOCUMENTS

| | | | |
|---|---|---|---|
| 4,733,665 | A | 3/1988 | Palmaz |
| 4,990,151 | A | 2/1991 | Wallsten |
| 5,087,244 | A | 2/1992 | Wolinsky et al. |
| 5,545,208 | A | 8/1996 | Wolff et al. |
| 5,549,635 | A | 8/1996 | Solar |
| 5,628,784 | A | 5/1997 | Strecker |
| 5,690,644 | A | 11/1997 | Yurek et al. |

(Continued)

FOREIGN PATENT DOCUMENTS

| | | |
|---|---|---|
| DE | 19509464 | 6/1996 |
| EP | 0716836 | 6/1996 |

(Continued)

OTHER PUBLICATIONS

U.S. Appl. No. 11/064,692, mailed May 10, 2013, Office Action.

(Continued)

*Primary Examiner* — Ryan Severson
*Assistant Examiner* — David Eastwood
(74) *Attorney, Agent, or Firm* — Workman Nydegger; Jonathan D. Feuchtwang

(57) ABSTRACT

The present invention relates to a stent delivery system and a process for mounting a stent onto a delivery system. More specifically, the present invention relates to a method of loading a stent onto a balloon and mounting the stent balloon assembly onto a catheter. The premounting of the stent onto the balloon subassembly allows the stent to be crimped in a way that the crimping recoil can be compensated and stent retention is kept at a maximum.

4 Claims, 2 Drawing Sheets

(56) References Cited

U.S. PATENT DOCUMENTS

| | | | |
|---|---|---|---|
| 5,716,393 A | 2/1998 | Lindenberg et al. | |
| 5,728,068 A | 3/1998 | Leone et al. | |
| 5,759,474 A | 6/1998 | Rupp et al. | |
| 5,776,140 A | 7/1998 | Cottone | |
| 5,782,839 A | 7/1998 | Hart et al. | |
| 5,836,965 A | 11/1998 | Jendersee et al. | |
| 5,860,966 A | 1/1999 | Tower | |
| 5,871,468 A | 2/1999 | Kramer et al. | |
| 5,893,852 A | 4/1999 | Morales | |
| 5,920,975 A | 7/1999 | Morales | |
| 5,976,181 A | 11/1999 | Whelan et al. | |
| 5,980,530 A | 11/1999 | Willard et al. | |
| 6,074,381 A | 6/2000 | Dinh et al. | |
| 6,082,990 A | 7/2000 | Jackson et al. | |
| 6,106,530 A | 8/2000 | Harada | |
| 6,110,180 A | 8/2000 | Foreman et al. | |
| 6,120,522 A | 9/2000 | Vrba et al. | |
| 6,141,855 A * | 11/2000 | Morales | 29/516 |
| 6,159,227 A | 12/2000 | Di Caprio et al. | |
| 6,264,683 B1 | 7/2001 | Stack et al. | |
| 6,267,776 B1 | 7/2001 | O'Connell | |
| 6,280,412 B1 | 8/2001 | Pederson, Jr. et al. | |
| 6,296,655 B1 | 10/2001 | Gaudoin et al. | |
| 6,352,547 B1 | 3/2002 | Brown et al. | |
| 6,481,262 B2 | 11/2002 | Ching et al. | |
| 6,510,722 B1 | 1/2003 | Ching et al. | |
| 6,517,559 B1 | 2/2003 | O'Connell | |
| 6,551,303 B1 | 4/2003 | Van Tassel et al. | |
| 6,764,504 B2 * | 7/2004 | Wang et al. | 623/1.11 |
| 6,769,161 B2 | 8/2004 | Brown et al. | |
| 6,863,683 B2 * | 3/2005 | Schwager et al. | 623/1.11 |
| 7,347,869 B2 | 3/2008 | Hojeibane et al. | |
| 7,470,281 B2 * | 12/2008 | Tedeschi | 623/1.11 |
| 7,722,663 B1 * | 5/2010 | Austin | 623/1.22 |
| 8,236,039 B2 | 8/2012 | Mackiewicz | |
| 8,309,023 B2 * | 11/2012 | Ramzipoor et al. | 422/28 |
| 2001/0001128 A1* | 5/2001 | Holman et al. | 623/1.11 |
| 2002/0007207 A1 | 1/2002 | Shin et al. | |
| 2002/0035774 A1* | 3/2002 | Austin | 29/516 |
| 2002/0068967 A1 | 6/2002 | Drasler et al. | |
| 2002/0138127 A1* | 9/2002 | Stiger et al. | 623/1.11 |
| 2003/0040772 A1 | 2/2003 | Hyodoh et al. | |
| 2003/0097172 A1 | 5/2003 | Shalev et al. | |
| 2003/0208227 A1 | 11/2003 | Thomas | |
| 2003/0212450 A1 | 11/2003 | Schlick | |
| 2004/0073155 A1 | 4/2004 | Laufer et al. | |
| 2004/0133263 A1 | 7/2004 | Dusbabek et al. | |
| 2005/0096735 A1 | 5/2005 | Hojeibane et al. | |
| 2005/0143752 A1 | 6/2005 | Schwager et al. | |
| 2005/0154450 A1* | 7/2005 | Larson et al. | 623/1.42 |
| 2005/0183259 A1 | 8/2005 | Eidenschink et al. | |
| 2005/0203606 A1 | 9/2005 | VanCamp | |
| 2005/0267408 A1 | 12/2005 | Grandt et al. | |
| 2005/0283962 A1* | 12/2005 | Boudjemline | 29/433 |
| 2006/0004328 A1 | 1/2006 | Joergensen et al. | |
| 2006/0020285 A1 | 1/2006 | Niermann | |
| 2006/0030923 A1 | 2/2006 | Gunderson | |
| 2006/0041271 A1 | 2/2006 | Bosma et al. | |
| 2006/0047336 A1 | 3/2006 | Gale et al. | |
| 2006/0229712 A1* | 10/2006 | Wilson et al. | 623/1.42 |
| 2006/0287708 A1* | 12/2006 | Ricci et al. | 623/1.15 |
| 2006/0288561 A1* | 12/2006 | Roach et al. | 29/508 |
| 2007/0208370 A1 | 9/2007 | Hauser et al. | |
| 2007/0255388 A1 | 11/2007 | Rudakov et al. | |
| 2008/0097570 A1 | 4/2008 | Thornton et al. | |
| 2008/0208118 A1 | 8/2008 | Goldman | |
| 2009/0076448 A1 | 3/2009 | Consigny et al. | |
| 2009/0105747 A1 | 4/2009 | Chanduszko et al. | |
| 2009/0187211 A1 | 7/2009 | Mackiewicz | |
| 2009/0292347 A1* | 11/2009 | Asmus et al. | 623/1.11 |
| 2010/0152765 A1 | 6/2010 | Haley | |
| 2011/0106234 A1 | 5/2011 | Grandt | |
| 2011/0257675 A1 | 10/2011 | Mackiewicz | |
| 2012/0259402 A1 | 10/2012 | Grandt | |

FOREIGN PATENT DOCUMENTS

| | | |
|---|---|---|
| EP | 0935952 | 8/1999 |
| EP | 1637177 | 3/2006 |
| EP | 2196174 | 6/2010 |
| EP | 2322118 | 5/2011 |
| WO | WO 99/16382 | 4/1999 |
| WO | WO 99/55255 | 11/1999 |
| WO | WO 00/78249 | 12/2000 |
| WO | WO 01/05462 | 1/2001 |
| WO | WO 01/21110 | 3/2001 |
| WO | WO 2004/047681 | 6/2004 |
| WO | WO 2007/061927 | 5/2007 |
| WO | WO 2008/024491 | 2/2008 |
| WO | WO 2008/024621 | 2/2008 |
| WO | WO 2009/066330 | 5/2009 |
| WO | WO 2009/086205 | 7/2009 |
| WO | WO 2010/066446 | 6/2010 |
| WO | WO 2011/050979 | 5/2011 |

OTHER PUBLICATIONS

U.S. Appl. No. 61/016,266, filed Dec. 21, 2007, Mackiewicz.
U.S. Appl. No. 61/138,455, Dec. 17, 2008, Haley.
U.S. Appl. No. 09/957,216, mailed Jun. 10, 2003, Office Action.
U.S. Appl. No. 09/957,216, mailed Sep. 26, 2003, Office Action.
U.S. Appl. No. 09/957,216, mailed Jun. 14, 2004, Office Action.
U.S. Appl. No. 09/957,216, mailed Nov. 4, 2004, Notice of Allowance.
U.S. Appl. No. 11/064,692, mailed Feb. 21, 2008, Office Action.
U.S. Appl. No. 11/064,692, mailed Oct. 14, 2008, Office Action.
U.S. Appl. No. 11/064,692, mailed Mar. 31, 2009, Office Action.
U.S. Appl. No. 11/064,692, mailed Nov. 23, 2009, Office Action.
U.S. Appl. No. 11/064,692, mailed Mar. 29, 2011, Office Action.
U.S. Appl. No. 11/064,692, mailed Aug. 2, 2011, Office Action.
U.S. Appl. No. 12/338,980, mailed Aug. 2, 2010, Office Action.
U.S. Appl. No. 12/338,980, mailed Oct. 27, 2010, Office Action.
U.S. Appl. No. 12/338,980, mailed Mar. 1, 2011, Office Action.
U.S. Appl. No. 12/338,980, mailed Apr. 3, 2012, Notice of Allowance.
U.S. Appl. No. 12/338,980, mailed May 25, 2012, Notice of Allowance.
U.S. Appl. No. 12/338,981, mailed Aug. 2, 2010, Office Action.
U.S. Appl. No. 12/338,981, mailed Oct. 27, 2010, Office Action.
U.S. Appl. No. 12/338,981, mailed Mar. 2, 2011, Office Action.
U.S. Appl. No. 12/537,097, mailed Dec. 15, 2011, Office Action.
U.S. Appl. No. 12/537,097, mailed Feb. 3, 2012, Office Action.
U.S. Appl. No. 12/537,097, mailed Jun. 27, 2012, Office Action.
U.S. Appl. No. 12/609,513, mailed Mar. 12, 2012, Office Action.
U.S. Appl. No. 12/609,513, mailed Aug. 24, 2012, Office Action.
U.S. Appl. No. 12/609,513, mailed Feb. 1, 2013, Office Action.
U.S. Appl. No. 13/151,893, mailed Jan. 27, 2012, Office Action.
U.S. Appl. No. 13/151,893, mailed Apr. 3, 2012, Office Action.

* cited by examiner

PROCESS FOR LOADING A STENT ONTO A STENT DELIVERY SYSTEM

CROSS-REFERENCE TO RELATED APPLICATIONS

This Patent Application is a U.S. National Stage of International Application No. PCT/EP2009/008886, filed on Dec. 11, 2009, which claims priority to European Application No. 08021665.8, filed on Dec. 12, 2008, the disclosures of which are incorporated herein by reference in their entireties.

FIELD OF THE INVENTION

The present invention relates to a stent delivery system as well as a process for mounting a stent onto a balloon. More specifically, the present invention relates to a method of increasing stent retention of a balloon expandable stent on a balloon of a balloon catheter by compensating for crimping recoil.

BACKGROUND OF THE INVENTION

A stent is commonly used alone or in conjunction with angioplasty to ensure patency through a patient's stenosed vessel. Stents overcome the natural tendency of the vessel walls of some patients to restenose after angioplasty. A stent is typically inserted into a vessel, positioned across a lesion, and then expanded to create or maintain a passageway through the vessel, thereby restoring near-normal blood flow through the vessel.

A variety of stents are known in the art, including self-expandable and expandable stents, as well as wire braid stents. One such stent is described, for example, in U.S. Pat. No. 4,733,665 to Palmaz. Expandable stents are typically delivered to treatment sites on delivery devices, such as balloon catheters or other expandable devices. Balloon catheters may comprise a balloon having a collapsed delivery configuration with wings that are wrapped and folded about the catheter. An expandable stent is then disposed over the balloon and crimped into a collapsed delivery configuration about the balloon by compressing the stent onto the balloon. The stent and balloon assembly may then be delivered, using well-known percutaneous techniques, to a treatment site within the patient's vasculature, for example, within the patient's coronary arteries. Once the stent is positioned across a lesion at the treatment site, it is expanded to a deployed configuration by inflating the balloon. The stent contacts the vessel wall and maintains a path for blood flow through the vessel.

Significant difficulties have been encountered during stent delivery and deployment, including difficulty in maintaining the stent on the balloon and in achieving symmetrical expansion of the stent when deployed. In positioning a balloon expandable stent on the delivery catheter over the fluid expandable balloon, the stent must be smoothly and evenly crimped to closely conform to the overall profile of the catheter and the unexpanded balloon. It has been noted that, due to physical properties of the material used in manufacturing the stent (e.g. stainless steel, tantalum, niobium, platinum, cobalt, chromium or alloys thereof) there is a certain amount of "recoil" of the stent despite the most careful and firm crimping. That is the stent evidences a tendency to slightly open up from the fully crimped position and once the crimping force has been released. For example, in the typical stent delivery and deployment assembly, if the stent has been fully crimped to a first diameter, the stent has been observed to open up or recoil to a second diameter which is approximately 1% to 10% greater than the first diameter. This phenomenon has been characterized as "crimping recoil". Due to crimping recoil to this slightly enlarged diameter, it can be understood that the stent tends to evidence a certain amount of looseness from its desired close adherence to the overall profile of the underlying catheter and balloon. That is, the stent tends to have a perceptible relatively slack fit in its mounted and crimped position. During delivery, the stent can thus tend to slip and dislocate from its desired position on the catheter or even become separate from the catheter, requiring further intervention by the physician.

The degree of crimping recoil highly depends on the stent material as well as the stent design itself. Presently there is a desire to manufacture stents not only from stainless steel but also from new materials like e.g. cobalt chromium alloys and niobium tantalum alloys. These new materials show increased strength and radiopacity over prior known stent materials and thus allow reduction of wall thickness of the stent struts while the stent's radial force and radio-visibility stays the same. Since reduction of strut thickness has clinically shown to reduce in-stent-restenosis there is a great interest in using these novel stent materials in stent manufacturing. The tradeoff of the increased strength of these alloys is that they often show increased recoil behaviour over the prior known stent materials.

Several techniques have been developed to more securely anchor the stent to the balloon and to ensure more symmetrical expansion. These include plastically deforming the stent so that it is crimped onto the balloon, and sizing the stent such that its internal diameter provides an interference fit with the outside diameter of the balloon catheter. Such techniques have several drawbacks, including less than optimal securement of the stent to the balloon. Consequently, the stent may become prematurely dislodged from the balloon during advancement of the stent delivery system to the treatment site.

Stent delivery systems utilizing a removable sheath disposed over the exterior surface of the stent, which is removed once the stent is positioned at the treatment site, have also been proposed, for example, in U.S. Pat. No. 5,690,644 to Yurek et al. Such systems may be used with or without retainer rings and are intended to protect the stent during delivery and to provide a smooth surface for easier passage through the patient's vasculature. However, the exterior sheath increases the crossing profile of the delivery system while decreasing flexibility, thereby decreasing the ability of the device to track through narrowed and tortuous anatomy.

U.S. Pat. No. 6,106,530 to Harada describes a stent delivery device comprising a balloon catheter having stoppers disposed proximal and distal of a balloon onto which a stent is affixed for delivery. The stoppers are separate from the balloon and maintain the stent's position in relation to the balloon during delivery. As with the removable sheaths discussed previously, the stoppers are expected to increase delivery profile and decrease flexibility of the stent/balloon system.

U.S. Pat. No. 6,110,180 to Foreman et al. provides a catheter with a balloon having pre-formed, outwardly-extending protrusions on the exterior of the balloon. A stent may be crimped onto the balloon such that the protrusions extend into the gaps of the stent, thereby securing the stent about the balloon for delivery. A drawback to this device is the added complexity involved in manufacturing a balloon with pre-formed protrusions. Additionally, if the protrusions are not formed integrally with the balloon, there is a risk that one or more of the protrusions may detach during deployment of the stent. The protrusions may also reduce flexibility in the delivery configuration, thereby reducing ability to track through tortuous anatomy.

U.S. Pat. No. 6,159,227 to Di Caprio et al. provides a catheter with a securement means such as a corrugated tube mounted on the inner shaft underneath the balloon to compensate for crimp recoil and provide increased stent friction. However, similar to what was discussed above with regard to the exterior sheath; the corrugated tube increases the crossing profile of the delivery system while decreasing flexibility, thereby decreasing the ability of the device to track through narrowed and tortuous anatomy.

In each of the devices and methods described above, the balloon is pre-mounted onto a catheter shaft and the stent is then crimped down onto the balloon and catheter shaft. Typically, catheters shafts are constructed of polymeric materials, and thus compress slightly and also re-coil much like the stent does as described above, thereby contributing to the problem.

In view of the drawbacks associated with previously known methods and apparatus for loading a stent onto a stent delivery system, it would be desirable to provide methods and apparatus that overcome those drawbacks.

It would be desirable to provide methods and apparatus for loading a stent onto a stent delivery system that enhance positional stability of the stent during delivery. It would further be desirable to provide methods and apparatus for loading a stent onto a stent delivery system wherein the delivery system comprises a crossing profile and flexibility suitable for use in tortuous and narrowed anatomy. It would still further be desirable to provide methods and apparatus for loading a stent onto a stent delivery system that provide a substantially symmetrical expansion of the stent at deployment.

SUMMARY OF THE INVENTION

In view of the foregoing, it is an object of the present invention to provide a stent delivery system with increase stent retention as well as methods and apparatus for loading a stent onto a delivery system and deployment that overcome drawbacks associated with previously known methods and apparatus.

In accordance with one embodiment of the present invention there is provided a stent delivery system having a contracted delivery configuration and an expanded deployed configuration, the stent delivery system comprising, a delivery catheter having an inflatable balloon, and a stent being disposed about the balloon, wherein the stent in its contracted delivery configuration exerts a constant elastic force on the balloon.

In accordance with the present invention there is provided a method of fabricating a stent delivery system comprising the steps of: (1) providing a balloon comprising a cylindrical balloon body having a distal and a proximal balloon cone and a proximal and a distal balloon sleeve, (2) providing a stent which can be transformed between a first configuration to a second collapsed configuration, (3) disposing the stent about at least a portion of the cylindrical balloon body, (4) applying a crimping force to the stent, and (4) mounting the balloon stent assembly onto a catheter.

It is an object to provide methods and apparatus for loading a stent onto a stent delivery system that enhance positional stability of the stent during delivery.

It is an object to provide methods and apparatus for loading a stent onto a stent delivery system wherein the delivery system comprises a crossing profile and flexibility suitable for use in tortuous and narrowed anatomy.

It is also an object to provide methods and apparatus for loading a stent onto a stent delivery system that provide a substantially symmetrical expansion of the stent at deployment.

These and other objects of the present invention are achieved by providing methods and apparatus for mounting a stent onto a balloon and mounting the balloon stent assembly onto a catheter. In a preferred embodiment, the stent is a balloon expandable stent and is manufactured in a fully-expanded state or in an intermediate-expanded state (i.e., having a diameter smaller than its fully-expanded, deployed diameter, but larger than its compressed delivery diameter).

The medical balloon is dimensioned for attachment to a catheter preassembly in order to result in a balloon dilatation catheter as for example described in U.S. Pat. Appl. 2005/0267408, or U.S. Pat. Appl. 2006/0004328 which are herewith incorporated by reference. In a preferred embodiment, the balloon comprises a cylindrical balloon body, a distal and a proximal balloon cone and a proximal and a distal balloon sleeve. The sleeves of the medical balloon are prefixed to a crimping mandrel. The crimping mandrel is configured to allow in/deflation of the balloon once fixated to the mandrel. The stent is then disposed about at least a portion of the cylindrical balloon body. Subsequently the stent is crimped onto the balloon by any suitable crimping technique known in the art. As during crimping the balloon is not mounted on the final catheter assembly but on a crimping mandrel, the diameter to which the stent is crimped down can be easily adjusted by actuation of the crimping tool and/or by adjusting the dimensions of the portion of the crimping mandrel lying underneath the balloon. The crimp diameter is adjusted to be smaller than the final crimped stent diameter is intended to be. Thus, the naturally occurring stent crimping recoil will be compensated by a respective "over crimping" of the stent on the balloon. After the stent is crimped on the balloon, the crimping mandrel is removed and the balloon stent assembly is mounted on a catheter preassembly to result in the final stent delivery device or system. In a preferred embodiment, the distal balloon sleeve of the balloon stent subassembly will be sealingly attached to a distal portion of an guide wire tube of the catheter subassembly, while the proximal balloon sleeve of the balloon stent subassembly will be sealingly attached to the distal portion of the in/deflation tube or outer tube of the catheter subassembly to allow the medical balloon to be inflated for placement of the stent in the target vessel. Preferably, the outer diameter of the guide wire tube is slightly larger than the average inner diameter left open inside the balloon after the stent has been crimped thereon. This can be achieved for example by using a mandrel with an outer diameter underneath the balloon smaller than the outer diameter of the guide wire tube of the catheter subassembly. Once the balloon with the stent crimped thereon, also referred to as balloon stent subassembly, is mounted on the catheter subassembly the stent crimped on the balloon exerts a constant elastic force onto the balloon and the guide wire tube. This constant elastic force leads to a maximum of frictional force between the balloon and the stent.

In conventional crimping processes the stent is crimped onto the balloon of a balloon dilatation catheter to form the final stent delivery device. In these methods the stent is pressed onto the balloon and the friction forces merely result from the press fit or interference fit between balloon and stent, the stent cannot exert an elastic force onto the guide wire tube. In conventional stent delivery systems stent retention can only be achieved by an unfolding of the balloon to a greater extend than the stent crimping recoil forces the stent to open.

Apparatus and method of the present invention may be used with a variety of prior art stents, such as balloon expandable stents, and may include tubular slotted stents, connected stents, articulated stents, multiple connected or non-connected stents, and bi-stable stents. In addition to apparatus and methods of production, methods of using the apparatus of the present invention are provided.

BRIEF DESCRIPTION OF THE DRAWINGS

Further features of the invention, its nature and various advantages will be more apparent from the following detailed description of the preferred embodiments, taken in conjunction with the accompanying drawings, in which like reference numerals refer to like parts throughout, and in which.

DETAILED DESCRIPTION OF THE INVENTION

The present invention is directed to a stent delivery system having a contracted delivery configuration and an expanded deployed configuration, the stent delivery system comprising a delivery catheter having an inflatable balloon; and a stent being disposed about the balloon, wherein the stent in its contracted delivery configuration exerts a constant elastic force on the balloon. The present invention further comprises methods and apparatus for mounting a crimped stent and balloon assembly onto a delivery system. More specifically, the present invention provides methods and apparatus for fabricating a stent delivery system comprising a delivery catheter having an inflatable balloon; and a stent being disposed about the balloon, wherein the stent in its contracted delivery configuration exerts a constant elastic force on the balloon. The methods for fabricating a stent delivery system comprise providing a balloon comprising a cylindrical balloon body, a distal and a proximal balloon cone and a proximal and a distal balloon sleeve, providing a stent which can be transformed from a first diameter or collapsed configuration to a second diameter or expanded configuration, disposing a within a lumen of cylindrical balloon body, wherein the mandrel includes a reduced diameter portion, disposing the stent about at least a portion of the cylindrical balloon body, crimping the stent and balloon, and subsequently mounting the balloon stent assembly or also called crimped balloon assembly onto a catheter.

Figure 1:
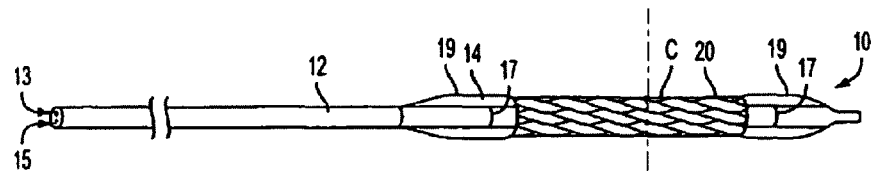
FIG. 1 is a side view of a stent delivery system in accordance with the present invention.

With reference to FIG. 1 an apparatus in accordance with the present invention is described. As seen in FIG. 1, stent delivery system 10, illustratively shown in a collapsed delivery configuration, comprises balloon expandable stent 20 loaded on balloon 14 of delivery catheter 12. Stent 20 comprises an illustrative balloon expandable stent and may be replaced with other stents known in the art.

Delivery catheter 12 preferably includes markers 17 disposed distal of and proximal to stent 20 that facilitate placement of stent 20 on balloon 14, and that facilitate positioning of stent delivery system 10 at a treatment site within a patient's vasculature. Markers 17 are preferably radiopaque and fabricated from a radiopaque material, such as platinum, platinum iridium alloys or gold. Catheter 12 preferably also comprises guide wire lumen 13 and inflation lumen 15, which is coupled to balloon 14. It is preferred that the markers 17 are flush with or substantially flush with and outer diameter of the delivery catheter 12. It is further contemplated that the markers 17 may be constructed of a radiopaque ink or radiopaque polymeric material which may be printed onto or formed within or onto the delivery catheter 12.

Balloon 14 is expandable by injection of a suitable medium, such as carbon dioxide, saline, or other biocompatible fluids and gasses via inflation lumen 15. Balloon 14 preferably expands stent 20 to a deployed configuration under application of pressure in the range of about 3-14 atm. Additionally, balloon 14 preferably has a rated burst pressure above 10 atm, and even more preferably between about 12-14 atm. Balloon 14 may be fabricated from a variety of materials, including polyamides like e.g. Nylon, or modified polyamides, polyethylene terephthalate, polyethylene, and polyether/polyamide block copolymers, such as PEBAX or blends and multilayers thereof.

Additionally, balloon 14 may be fabricated from an elastomeric polyester block copolymer having an aromatic polyester hard segment and an aliphatic polyester soft segment, such as "Pelprene", which is marketed by the Toyobo Corporation of Osaka, Japan. Balloon 14 also may be fabricated from a copolymer having a polybutylene terephthalate hard segment and a long chain of polyether glycol soft segment, such as "Hytrel" from the DuPont Corporation of Wilmington, Del.

Illustrative stent 20 may be fabricated from a variety of materials, including polymers and metals or a combination thereof (for example and not limitation stainless steel, tantalum, niobium, platinum, cobalt, chromium or alloys thereof), and may comprise any of a variety of prior art stents, such as balloon expandable stents, including tubular slotted stents, connected stents, articulated stents, multiple connected or non-connected stents, and bi-stable stents. Stent 20 also may include external coating C configured to retard restenosis or thrombus formation in the vessel region surrounding the stent. Alternatively, coating C may deliver therapeutic agents into the patient's blood stream or vessel wall.

The delivery catheter according to the present invention is preferably a catheter that is guided over a guide wire to a target site in a patient's vessel. The catheter may be an over-the-wire type catheter or a rapid-exchange catheter. Further, the configuration of the guide wire tube and the inflation lumen tube may be a coaxial constriction, a side-by-side construction, a smiley lumen or any variation or combination thereof.

Figure 2:
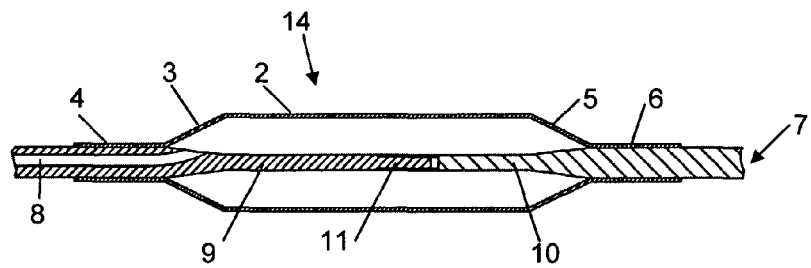
FIG. 2 is a side view of the medical balloon prefixed to a crimping mandrel.

Referring now to FIGS. 2-5 there is shown a method of producing the stent delivery system 10 in accordance with the present invention. As shown in FIG. 2, a balloon 14 is provided, the balloon comprises a cylindrical balloon body 2 having a distal balloon cone 5 and a proximal balloon cone 3 and a proximal balloon sleeve 4 and a distal balloon sleeve 6. The balloon may be constructed of any of the materials described above. As shown in FIG. 2, a crimping mandrel 7 is disposed through a lumen of the balloon.

The crimping mandrel 7 is formed from at least two parts, a proximal crimping mandrel portion 9 and a distal crimping mandrel portion 10 that are detachably connected at a joint 11. The outer diameter of the mandrel's middle portion that is located underneath the balloon 14 is less than the outer diameter underneath the balloon-sleeves 4, 6 and less than the outer diameter of the inner body/guide wire lumen that is desired to be mounted underneath the balloon. The outer diameter of the mandrel 7 underneath the proximal balloon sleeve 4 corresponds to the inner diameter of the proximal balloon sleeve 4 whereas the outer diameter of the mandrel 7 underneath the distal balloon sleeve 6 corresponds to the inner diameter of the distal balloon sleeve 6. The joint 11 of the two crimping mandrel portions 9 and 10 is located at a position underneath the balloon where its outer diameter is minimal. One part of this mandrel 7, preferably the proximal part 9 comprises an inner lumen that can be used to in-/deflate the balloon for folding and embedding. The crimping mandrel 7 is used for folding the balloon and crimping/embedding the stent into the balloon as will be described in detail below.

The balloon 14 is sealingly attached to the crimping mandrel 7 in a liquid tight manner at both balloon-sleeves 4, 6 by either welding, adhesive bonding, by wrapping an elastic band or ring about the sleeve or simply by shaping of the mandrel such that interference between the mandrel and the balloon sleeve 4, 6 forms a fluid tight seal. Once the balloon 14 is fixed and sealed on the crimping mandrel 7, the balloon 14 can be inflated and deflated over the inflation lumen 8 of the crimping mandrel 7 to ensure that a fluid tight seal is formed between the balloon sleeves and the mandrel. In a preferred embodiment the balloon 14 gets folded or pleated around the crimping mandrel 7 in order to obtain a small cross sectional profile of the balloon.

Generally, the crimping mandrel 7 should not have any sharp edges so that it cannot scratch the balloon 14. It may entirely consist of polymer (e.g. Polyimide, PEEK or PTFE) or of a metallic core that is polished or entirely or partly coated e.g. with Parylene, Polyimide, Teflon, or PTFE.

It is obvious to the person skilled in the art that the crimping mandrel 7 can be of various shapes and constructions. For example the mandrel can be of dog bone shape with a first distal outer diameter which is equal to the inner diameter of the distal balloon sleeve 6, a second outer diameter which is smaller that the first outer diameter and smaller than the outer diameter of the inner body of the catheter device and a third outer diameter which is equal to the inner diameter of the proximal balloon sleeve 4. Instead of a joint in the region of the smallest outer diameter, the mandrel may comprise a predetermined breaking point. In another preferred embodiment the mandrel 7 has a first distal outer diameter which is equal to the inner diameter of the distal balloon sleeve 6 and second outer diameter which is smaller than the first outer diameter. In the region underneath the proximal balloon sleeve, an additional removable ring or short tube with an outer diameter corresponding to the inner diameter of the proximal balloon sleeve 4 and an inner diameter configured to pressfit to the second diameter of the mandrel is provided to allow liquid tight sealing of the proximal and distal balloon sleeve 4, 6 to the crimping mandrel 7. Alternatively, the mandrel's outer diameter underneath the distal balloon sleeve 6 can be adapted to the inner diameter of the distal balloon sleeve 6 by an additional removable ring or short tube while the proximal diameter of the crimping mandrel 7 is fixed. Further, the mandrel 7 may have one constant outer diameter corresponding to the smallest diameter required underneath the cylindrical balloon body and removable adaptor rings or short tubes corresponding to the dimensions of distal and proximal balloon sleeves, respectively, will be employed to sealingly attach the balloon 14 to the crimping mandrel 7.

In another embodiment the mandrel may be configured as a two part mandrel wherein the two parts of the mandrel are not affixed to each other. In this embodiment the outer diameter of the first part of the mandrel corresponds to the inner diameter of the distal balloon sleeve and the outer diameter of the second part of the mandrel corresponds to the inner diameter of the proximal balloon sleeve in order to allow to sealingly attach the balloon 14 to the two parts of the mandrel. No part of the mandrel is located underneath the cylindrical balloon body 2, thus allowing a minimal crimping diameter.

Figure 3:
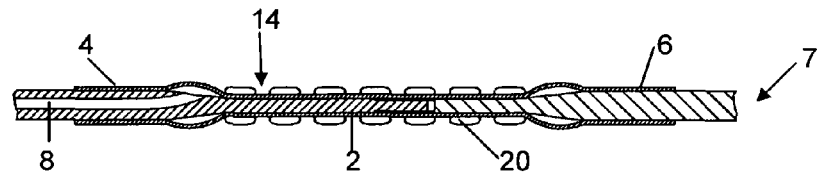
FIG. 3 depicts a side view of the stent crimped on the medical balloon, the medical balloon prefixed on a crimping mandrel.

Referring now to FIG. 3, there is shown the next step in forming a stent delivery catheter in accordance with the present invention. As shown in FIG. 3, a stent 20 is radially disposed about the balloon and mandrel assembly, wherein the stent 20, balloon 14 and the mandrel 7 is placed into a crimping device. The stent 20 can be transformed to a collapsed configuration from an expanded configuration. As shown, the stent is disposed over at least a portion of the cylindrical balloon body 2 of the optionally folded balloon 14 and the stent is crimped onto the balloon 14/crimping mandrel 7 assembly.

Crimping of the stent on the medical balloon is performed by standard crimping techniques as for example described in U.S. Pat. No. 5,836,965 to Jendersee et al; U.S. Pat. Appl. No. 2005/0143752 to Schwager et al; or U.S. Pat. No. 5,976,181 to Whelan et al, which are herewith incorporated by reference.

Once the stent 20 is crimped on the balloon 14 and preferably also embedded into the balloon 14 the crimping mandrel 7 can be split into its two parts 9, 10 and both crimping mandrel portions 9, 10 can be retrieved in proximal and distal direction, respectively. This results in a stent balloon preassembly 24 as shown in FIG. 4A wherein the stent is crimped down to the cylindrical balloon portion 2 to an inner stent diameter preferably smaller than the inner diameter of the proximal and/or distal balloon sleeve 4, 6.

The smaller diameter of the crimping mandrel 7 in its middle portion is adjusted to compensate for the crimp-recoil of the stent 20. With the crimping tongs of a commonly known crimping tool fully closed, the stent 20 and balloon material 14 will create a tight fit on the crimping mandrel 7. As soon as the crimping tongs get released the recoil of the stent material will cause the stent to open up again slightly and loosen the grip of the stent 20 and balloon-material 14 to the mandrel 7. Ideally the crimping mandrel's smaller diameter is dimensioned in a way that the stent 20 just opens up that much that its inner diameter in combination with the balloon material is slightly less than the outer diameter of the inner body 23 that is intended to be mounted inside the balloon 14. In any case crimping mandrel's smaller outer diameter in its middle portion is smaller than the outer diameter of the inner body 23 of the catheter device 12.

Figure 4A:
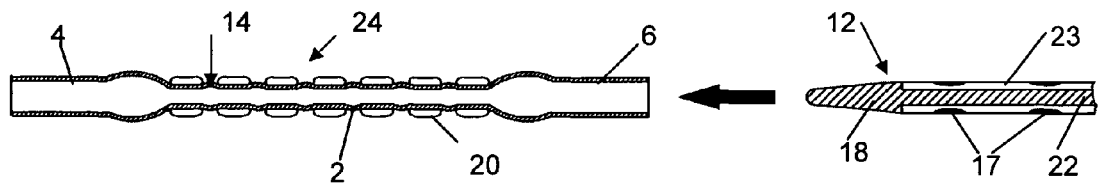
FIG. 4A is a side view of the crimped stent balloon subassembly.
Figure 4B:
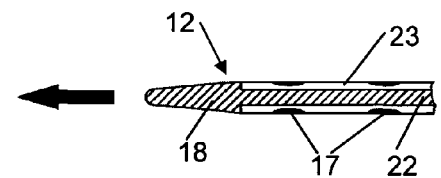
FIG. 4B depicts a side view of the distal portion of a catheter shaft subassembly positioned on a assembly mandrel.

As shown in FIGS. 4A and 4B, the next step in accordance with the present invention is to secure the crimped balloon/stent assembly about a catheter shaft 12. Referring now to FIG. 4B there is shown a distal end portion of a catheter subassembly 12 in accordance with the present invention as described above. A mandrel is inserted into the guidewire lumen of the catheter subassembly 12, a distal end 18 of the mandrel is formed having a conical shape. The distal end of the catheter subassembly, including the mandrel 22, is disposed through the lumen of the crimped balloon/stent assembly as indicated by the arrow. Due to the elastic behaviour of the stent 20 and its crimped inner diameter of slightly less than the outer diameter of the inner tube 23, the stent 20 exerts a constant elastic force on the balloon 14 and the inner catheter body 23. Thereby a maximum of frictional force between the stent 20 and the balloon 14 is achieved resulting in a maximum of stent retention.

Figure 5:
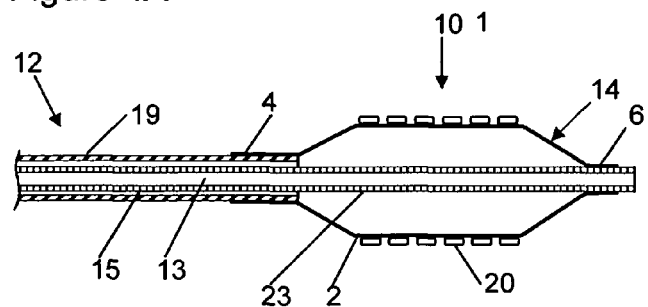
FIG. 5 is a side view of a stent delivery system according to the present invention in its expanded configuration.

Finally, the distal balloon sleeve 6 is attached to the inner body 23 and the proximal balloon sleeve 4 is attached to the outer body 19 of the catheter preassembly 12. For better illustration FIG. 5 shows a side view of a distal part of one embodiment of the stent delivery system according to the present invention in its expanded configuration. In this embodiment an over-the-wire or rapid-exchange catheter with a coaxial shaft configuration is illustrated, however any other catheter construction like side-by-side or smiley lumen may be employed. The distal balloon sleeve 6 of the balloon 14 carrying the stent 20 is sealingly attached to a distal portion of the inner tube or guide wire tube 23 of the catheter subassembly 12, whereas the proximal balloon sleeve 4 of the balloon is sealingly attached to the distal end of the outer tube 19 of the catheter subassembly 12. The attachment of the balloon to the catheter subassembly can be done for example and not for limitation by light welding, laser welding, hot jaw welding, hot air welding or by applying an adhesive.

In an alternative method of production of the stent delivery catheter according to the present invention, the outer body and proximal balloon sleeve may be attached to each other before the stent is disposed and crimped onto the balloon.

In a preferred embodiment the stent delivery catheter according to the present invention further comprises radiopaque markers 17 on the inner tube 23 underneath the stent 20 or adjacent to the stent ends. In a more preferred embodiment these radiopaque markers 17 do preferably consist of a polymeric material (e.g. barium sulphate dotted polymers) avoiding sharp edges as on commonly used metallic markers. Alternatively the metallic markers can be swaged with rounded edges and/or covered by a thin polymeric film. In an even more preferred embodiment the metallic or polymeric markers may be incorporated into the tube to result in a flush outer surface of the markers and the inner lumen tube. The markers can be very accurately positioned/adjusted to the position of the stent.

Referring now to FIGS. 6, a method of using stent delivery system 10 of the present invention is described. Stent delivery system 10 is disposed in a contracted delivery configuration with stent 20 disposed over balloon 14 of delivery catheter 12. The stent exerts a constant elastic force on the balloon 14. As seen in FIG. 6A, the distal end of catheter 12 is delivered to a target site T within a patient's vessel V using, for example, well-known percutaneous techniques. Target site T may, for example, comprise a stenosed region of vessel V. The radiopacity of markers 17 may facilitate positioning of system 10 at the target site. Alternatively, stent 20 or other portions of catheter 12 may be radiopaque to facilitate positioning.

Figure 6A:
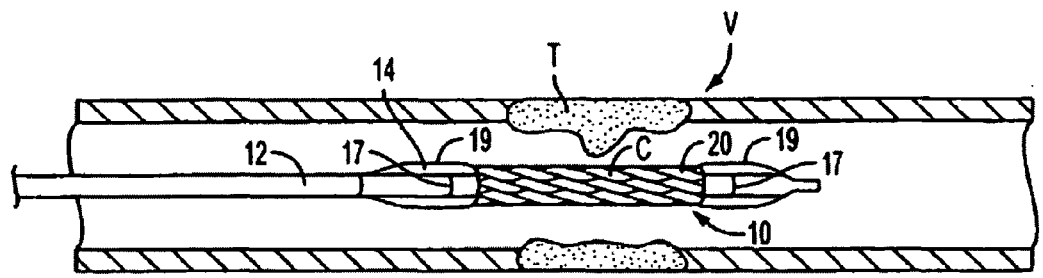
FIGS. 6A to 6D are side views, partially in section, of the stent delivery system of FIG. 1 disposed within a patient's vasculature, depicting a method of using the apparatus in accordance with the present invention.
Figure 6B:
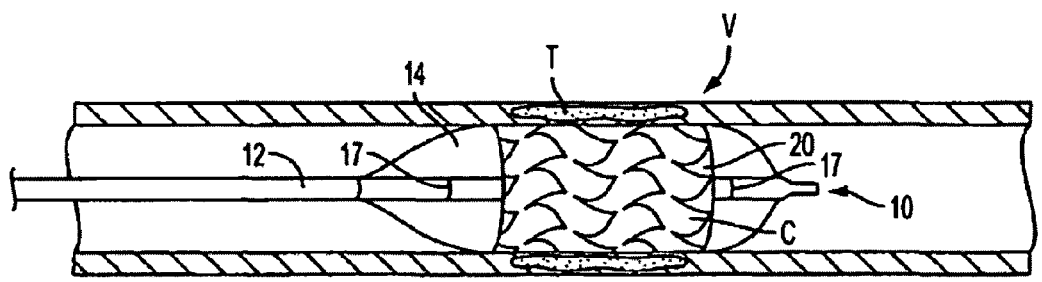
Figure 6C:
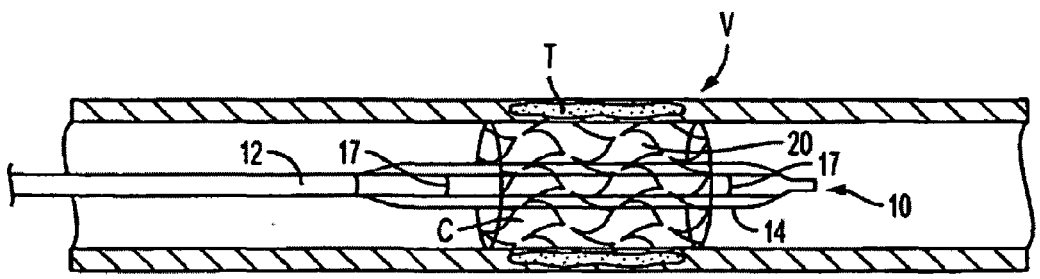
Figure 6D:
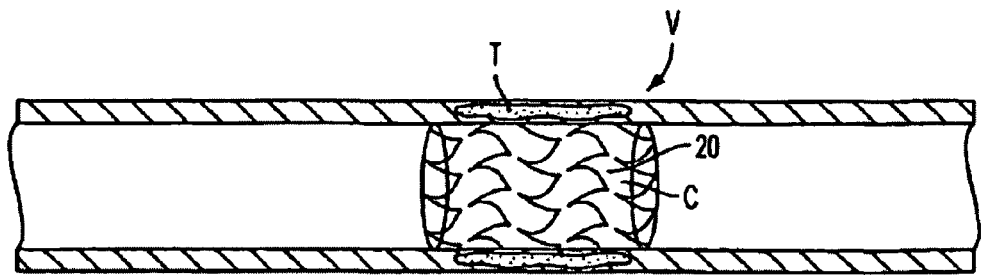

In FIG. 6B, balloon 14 is inflated, for example, via an inflation medium delivered through inflation lumen 15 of catheter 12. Stent 20 expands to the deployed configuration in which it contacts the wall of vessel V at target site T. Balloon 14 is then deflated, as seen in FIG. 6C, and delivery catheter 12 is removed from vessel V, as seen in FIG. 6D.

Stent 20 remains in place within vessel V in the deployed configuration in order to reduce restenosis and recoil of the vessel. Stent 20 also may comprise external coating C configured to retard restenosis or thrombus formation around the stent. Alternatively, coating C may deliver therapeutic agents into the patient's blood stream or a portion of the vessel wall adjacent to the stent.

Although preferred illustrative embodiments of the present invention are described hereinabove, it will be evident to those skilled in the art that various changes and modifications may be made therein without departing from the invention.

It is intended in the appended claims to cover all such changes and modifications that fall within the true spirit and scope of the invention.

The invention claimed is:

1. A method of fabricating a stent delivers system comprising:
    providing, a balloon comprising a cylindrical balloon body, a distal and a proximal balloon cone and a proximal and a distal balloon sleeve;
    providing a stent which can be transformed from a first diameter to a second diameter;
    disposing a mandrel within a lumen of the cylindrical balloon body, wherein the mandrel includes a reduced diameter portion;
    disposing the stent about a portion of the cylindrical balloon body;
    crimping the stent and balloon about the mandrel, thereby forming a crimped balloon assembly;
    removing the mandrel after crimping; and
    disposing the crimped assembly about a catheter subassembly comprising an inner body, thereby causing the stent in its contracted delivery configuration to exert a constant elastic three on the balloon and the inner body of the catheter device.

2. The method according to claim 1, wherein the mandrel is of dog bone shape with a first distal outer diameter which is equal to the inner diameter of the distal balloon sleeve, a second outer diameter which is smaller than the outer diameter of the inner body of the catheter device and a third outer diameter which is equal to the inner diameter of the proximal balloon sleeve and a joint or predetermined braking point in the region of the mandrel's smallest diameter.

3. The method according to claim 1, wherein the mandrel has an outer diameter smaller than the outer diameter of the inner body of the catheter device and further comprises at least one removable adaptor ring or short tube corresponding to the dimensions of distal and proximal balloon sleeves, respectively.

4. The method according to claim 1, wherein the mandrel is a two-part mandrel wherein the two parts of the mandrel are not affixed to each other, wherein an outer diameter of a first part of the mandrel corresponds to an inner diameter of the distal balloon sleeve and an outer diameter of a second part of the mandrel corresponds to an inner diameter of the proximal balloon sleeve.

* * * * *

UNITED STATES PATENT AND TRADEMARK OFFICE
CERTIFICATE OF CORRECTION

PATENT NO.      : 8,591,565 B2                                        Page 1 of 1
APPLICATION NO. : 13/133930
DATED           : November 26, 2013
INVENTOR(S)     : Axel Grandt It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this

Twenty-second Day of September, 2015

Michelle K. Lee
*Director of the United States Patent and Trademark Office*